(12) United States Patent
Lin et al.

(10) Patent No.: US 12,414,849 B2
(45) Date of Patent: Sep. 16, 2025

(54) IMPLANTABLE DEVICE

(71) Applicant: Biotyx Medical (Shenzhen) Co., Ltd., Shenzhen (CN)

(72) Inventors: Zhenjian Lin, Shenzhen (CN); Jun Hu, Shenzhen (CN); Hongtao Sun, Shenzhen (CN); Li Qin, Shenzhen (CN); Deyuan Zhang, Shenzhen (CN)

(73) Assignee: BIOTYX MEDICAL (SHENZHEN) CO, LTD., Shenzhen (CN)

( * ) Notice: Subject to any disclaimer, the term of this patent is extended or adjusted under 35 U.S.C. 154(b) by 776 days.

(21) Appl. No.: 16/648,801

(22) PCT Filed: Sep. 20, 2018

(86) PCT No.: PCT/CN2018/106714
§ 371 (c)(1),
(2) Date: Mar. 19, 2020

(87) PCT Pub. No.: WO2019/062638
PCT Pub. Date: Apr. 4, 2019

(65) Prior Publication Data
US 2020/0214822 A1 Jul. 9, 2020

(30) Foreign Application Priority Data
Sep. 30, 2017 (CN) .......................... 201710922803.6

(51) Int. Cl.
*A61L 31/10* (2006.01)
*A61F 2/04* (2013.01)
*A61L 31/14* (2006.01)

(52) U.S. Cl.
CPC ............... *A61F 2/04* (2013.01); *A61L 31/10* (2013.01); *A61L 31/14* (2013.01); *A61F 2002/041* (2013.01); *A61F 2002/047* (2013.01)

(58) Field of Classification Search
CPC .... A61F 2002/2839; A61F 2310/00473; A61F 2/82; A61F 2/28; A61F 2/04;
(Continued)

(56) References Cited

U.S. PATENT DOCUMENTS 8,277,833 B2 10/2012 Atanasoska et al.
9,265,866 B2 * 2/2016 Kramer-Brown ....... A61L 31/08
623/1.34
(Continued)

FOREIGN PATENT DOCUMENTS

CA 2885981 A1 * 10/2006 ............... A61F 2/82
CN 101180087 A 5/2008
(Continued)

OTHER PUBLICATIONS

Translation of description and also claims for CN 103526261 (Year: 2014).*
(Continued)

*Primary Examiner* — Brian E Pellegrino
(74) *Attorney, Agent, or Firm* — Maier & Maier, PLLC

(57) ABSTRACT

An implantable device including a matrix and a zinc-containing layer at least partially covering the substrate. The zinc-containing layer includes a zinc compound. The ratio of the mass of the zinc element in the zinc-containing layer to the surface area of the implantable device is 0.1-200 μg/mm2. The average porosity of the zinc-containing layer is 30% or less. By matching the ratio of the mass of zinc in the zinc-containing layer to the surface area of the implantable device with the average porosity of the zinc-containing layer, the release rate of zinc is controlled within a reasonable range so that the rate of formation of the zinc-containing substance is controlled such that the concentration of the zinc-containing substance accumulated in the tissue is higher than the concentration which inhibits the proliferation (Continued)

of smooth muscle cells, and is always lower than the toxic concentration which causes cell death.

16 Claims, 5 Drawing Sheets

(58) Field of Classification Search
CPC .......... A61F 2002/041; A61F 2002/047; A61F 2210/0009; A61F 2250/0023; A61F 2250/0067; A61F 2210/0076; A61L 31/10; A61L 31/082; A61L 31/16; C23C 2/06
USPC .............................................. 427/192, 255.33
See application file for complete search history.

(56) References Cited

U.S. PATENT DOCUMENTS

| 2004/0111144 | A1* | 6/2004 | Lawin ..................... | A61L 31/10 |
| | | | | 424/468 |
| 2009/0324684 | A1 | 12/2009 | Atanasoska et al. | |
| 2012/0316633 | A1* | 12/2012 | Flanagan .................. | A61F 2/82 |
| | | | | 623/1.42 |
| 2017/0106123 | A1* | 4/2017 | Weber ................... | A61L 31/146 |
| | | | | 623/1.46 |

FOREIGN PATENT DOCUMENTS

| CN | 101745147 | A | | 6/2010 | |
| CN | 101874751 | B | | 7/2013 | |
| CN | 103526261 | A | * | 1/2014 | |
| CN | 205964236 | U | | 2/2017 | |
| CN | 106806938 | A | | 6/2017 | |
| CN | 106902385 | A | | 6/2017 | |
| CN | 106955374 | A | | 7/2017 | |
| EP | 2425866 | A1 | | 3/2012 | |
| WO | 2004/037120 | A2 | | 5/2004 | |
| WO | WO-2009021209 | A2 | * | 2/2009 | ......... A61F 2/30767 |

OTHER PUBLICATIONS

McGuffie et al. Zinc oxide nanoparticle suspensions and layer-by-layer coatings inhibit staphylococcal growth, Jan. 2016, Nanomedicine: Nanotechnology, Biology and Medicine, V. 12, pp. 33-42. (Year: 2016).*
Extended European Search Report issued on Jun. 9, 2021, including the Supplementary European Search Report and the European Search Opinion, in connection with corresponding EP Application No. 18861575.1 (8pp.).
Chinese Office Action issued on Feb. 24, 2021, in connection with corresponding CN Application No. 201710922803.6 (15pp., including machine-generated English translation).
Jun Ma, et al., "Bioabsorbable zinc ion induced biphasic cellular responses in vascular smooth muscle cells", Scientific Reports, vol. 6, No. 1, Jul. 1, 2016, pp. 1-10 (10pp), at URL: https://www.nature.com/articles/srep26661.
Indian Office Action issued on May 29, 2021, in connection with corresponding IN Application No. 202017013817 (6pp).
International Search Report issued on Dec. 7, 2018 and Written Opinion in corresponding International application No. PCT/CN2018/106714; 9 pages.
Office Action issued on Aug. 31, 2022, in corresponding Chinese Application No. 201710922803.6, 15 pages.

* cited by examiner

IMPLANTABLE DEVICE

FIELD

The disclosure relates to the field of medical devices, and more particularly relates to an implantable device.

BACKGROUND

An implantable device is implanted into the body of a patient to repair a diseased lesion. For example, a vascular stent is implanted into a lesion to support a stenotic occlusion segment of a blood vessel, thereby achieving purposes of reducing elastic retraction and reshaping the blood vessel and keeping smooth blood flow of a lumen. After the vascular stent is implanted into the body of the patient, the treated blood vessel is likely to heal rapidly after local injury. In the process of "healing", the smooth muscle cells around the implantable device proliferate greatly, which is likely to cause the restenosis of the local vascular lumen. Restenosis is a common adverse reaction after stent intervention in clinical practice, which can even endanger the life and safety of the patient in severe cases. Therefore, it is necessary to inhibit the proliferation of smooth muscle cells in tissues around the implantable device clinically.

Research has shown that during the corrosion of a zinc-containing implantable device in an implanted body, zinc ions and other zinc-containing substances released from the implantable device can inhibit the proliferation of the smooth muscle cells around the device when reaching a certain concentration; therefore, the device can reduce the lumen stenosis rate of the implanting part. However, there is also evidence showing that zinc-containing devices implanted in the body release excessive amounts of zinc ions that will kill smooth muscle cells, and even endothelial cells and other normal tissue cells, ultimately leading to the tissue ulceration or necrosis at a site of implantation.

SUMMARY

In view of this, there is a need in the field to provide an implantable device which not only effectively inhibits the proliferation of smooth muscle cells around the implantable device and reduces the likelihood of restenosis, but also prevents zinc-containing substances from being accumulated to a high toxic concentration in the surrounding tissues to cause the death of smooth muscle cells, endothelial cells, and other normal cells after implantation.

An exemplary embodiment of an implantable device includes a substrate and a zinc-containing layer at least partially covering the substrate. A ratio of a mass of zinc elements in the zinc-containing layer to a surface area of the substrate is 0.1 to 200 μg/mm$^2$, and an average porosity of the zinc-containing layer is less than or equal to 30%.

In one embodiment, the ratio of the mass of zinc elements in the zinc-containing layer to the surface area of the substrate is 1 to 150 μg/mm$^2$, and the porosity of the zinc-containing layer is 0 to 10%.

In one embodiment, the content of the zinc elements in the zinc-containing layer is 1.4 percentage by weight (wt. %) to 80 wt. %.

In one embodiment, a thickness of the zinc-containing layer is 1 μm to 50 μm.

In one embodiment, the zinc compound is selected from at least one of zinc gluconate, zinc tartrate, zinc lactate, zinc carbonate, zinc hydroxide, zinc sulfate, zinc chloride, zinc phosphate, zinc nitrate, zinc glycyrrhizinate, zinc citrate, zinc amino acid, zinc acetate, sodium zincate, zinc sulfide, and zinc oxide.

In one embodiment, the number of layers of the zinc-containing layer is one or more.

In one embodiment, the zinc-containing layer further includes a polymer.

In one embodiment, the implantable device further includes a barrier layer. The barrier at least partially covers the zinc-containing layer.

In one embodiment, the implantable device further includes a barrier layer. The barrier layer at least partially covers the zinc-containing layer.

In one embodiment, the barrier layer contains a polymer.

In one embodiment, a sum of the thickness of the barrier layer and the thickness of the zinc-containing layer is less than or equal to 50 μm.

In one embodiment, the polymer is selected from at least one of a degradable polymer and a non-degradable polymer, or at least one of copolymers formed by at least one monomer forming the degradable polymer and at least one monomer forming the non-degradable polymer, wherein the degradable polymer is selected from at least one of poly-lactic acid, polyglycolic acid, polycaprolactone, polyethylene succinate, polybutylene succinate and poly(β-hydroxy-butyrate), and the non-degradable polymer is selected from at least one of polystyrene, polytetrafluoroethylene, polymethyl methacrylate, polycarbonate and polyethylene terephthalate.

In one embodiment, a weight-average molecular weight of the polymer is 100,000 to 500,000.

In one embodiment, the substrate is made of a degradable material, a non-degradable material, or a partially degradable material.

In one embodiment, the implantable device is a vascular stent, a biliary stent, an esophageal stent, a urethral stent, an airway stent, or a vena cava filter.

An exemplary implantable device includes a substrate and a zinc-containing layer at least partially covering a surface of the substrate. The ratio of the mass of the zinc elements in the zinc-containing layer to the surface area of the substrate is 0.1 to 200 μg/mm$^2$, and the average porosity of the zinc-containing layer is less than or equal to 30%. By matching the ratio of the mass of the zinc elements in the zinc-containing layer to the surface area of the substrate and the average porosity of the zinc-containing layer, a release rate of zinc is controlled within a reasonable range, and a generation rate of zinc-containing substances is controlled. So that when the implantable device is implanted into a body, the concentration of the zinc-containing substances accumulated in the tissues is greater than the concentration for inhibiting the proliferation of the smooth muscle cells, and is always less than the toxic concentration for causing the death of smooth muscle cells, endothelial cells or other normal tissue cells. Therefore, the above-described implantable device may effectively inhibit the proliferation of the tissues around the device and prevent ulceration or necrosis of the tissues around the device.

DETAILED DESCRIPTION

In order to make the technical features, objects and effects of the present disclosure more clearly understood, specific implementation modes are described in detail with reference to the accompanying drawings, but the scope of the present disclosure is not limited thereto.

An exemplary implantable device according to one implementation mode includes a substrate and a zinc-containing layer at least partially covering the substrate. The zinc-containing layer contains a zinc-containing compound. A ratio of a mass of zinc elements in the zinc-containing layer to a surface area of the substrate is 0.1 to 200 µg/mm², and an average porosity of the zinc-containing layer is less than or equal to 30%.

The substrate may be made of a degradable material, a non-degradable material, or a partially degradable material. For example, the degradable material may be polylactic acid, iron, etc., the non-degradable material may be stainless steel, cobalt chromium alloy, etc., and the partially degradable material may be a mixture of polylactic acid and polystyrene, etc.

The zinc-containing layer is a coating that at least partially covers the surface of the substrate and is formed by spraying the zinc compound onto the substrate. The zinc-containing layer contains the zinc compound. The zinc compound is selected from at least one of zinc gluconate, zinc tartrate, zinc lactate, zinc carbonate, zinc hydroxide, zinc sulfate, zinc chloride, zinc phosphate, zinc nitrate, zinc glycyrrhizinate, zinc citrate, zinc amino acid, zinc acetate, sodium zincate, zinc sulfide, and zinc oxide. When at least two zinc compounds are contained, there is no limitation to the mass ratio of the two or more zinc compounds.

When the zinc compound is a water-soluble compound, zinc exists in an ionic form in the zinc-containing layer. When the zinc compound is a water-insoluble compound, the zinc is covalently bonded with other elements in the zinc-containing layer.

The zinc-containing layer may be one-layer or multilayer. When the zinc-containing layer is multilayer, the zinc compounds contained in adjacent zinc-containing layers are different.

The mass of the zinc elements in the zinc-containing layer can be determined by atomic absorption spectrometry. It may be contemplated that the surface area of the substrate refers to a total surface area of the substrate, including the surface areas of outer surface, inner surface, and side surfaces of the substrate. Moreover, the surface area of the substrate does not include a surface area increased by surface roughness or voids in the material from which the substrate is made.

Figure 1:
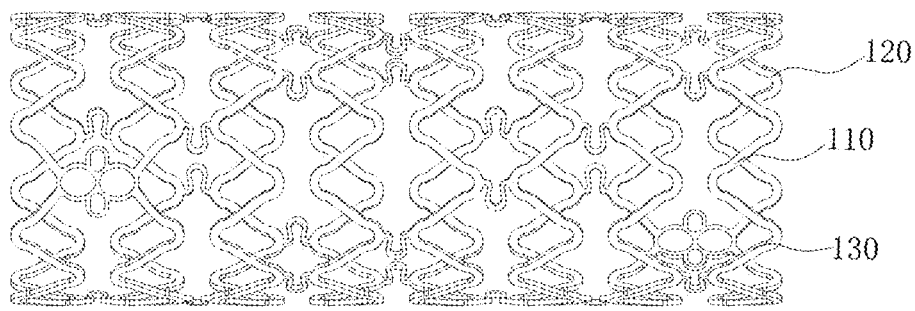
FIG. 1 is a schematic structural diagram of a lumen vascular stent according to an embodiment.

Referring to the exemplary embodiment in FIG. 1, an exemplary implantable device may be a lumen vascular stent 10. The exemplary lumen vascular stent 10 includes a substrate. A surface area of the substrate is a sum of the areas of outer surface 110, inner surface 120, and side surfaces 130, i.e., the surface area of the substrate refers to the sum of the areas of all surfaces of the substrate.

When the implantable device is implanted in the body, the zinc-containing layer contacts body fluid, the zinc compound in the zinc-containing layer is gradually released, and part of the zinc compound may also react with the body fluid to generate various zinc-containing corrosion products. The zinc compounds and various zinc-containing corrosion products released after the implantation of the implantable device are collectively called zinc-containing substances. Since the released zinc-containing substances may also be absorbed and metabolized by the body tissues, the zinc-containing substances can be gradually accumulated in the tissues around the device only when the release rate of the zinc-containing substances per unit time is greater than the metabolic rate of the body tissues. Finally, when the concentration of the zinc-containing substances accumulated in the tissues is higher than the lower limit of the concentration for inhibiting the proliferation of smooth muscle cells, the zinc-containing substances can inhibit the cell proliferation in the tissues around the device. At the same time, in order to avoid the death of the smooth muscle cells, endothelial cells or other normal tissue cells in the tissues around the device, and to prevent the tissue ulceration or necrosis, it is also desirable to control the concentration of zinc-containing substances accumulated in the tissues to be always lower than a toxic concentration causing the death of smooth muscle cells and other normal tissue cells.

Since the metabolic rate of the tissues to the zinc-containing substances is substantially constant, the concentration of the zinc-containing substances accumulated in the surrounding tissues is related to the release rate of zinc in the zinc-containing layer. The release rate of the zinc is related to the ratio of the mass of zinc elements in the zinc-containing layer to the surface area of the implantable device and the average porosity of the zinc-containing layer.

The ratio of the mass of zinc elements in the zinc-containing layer to the surface area of the implantable device is simply referred to as the mass-to-surface area ratio of the zinc. The low mass-to-surface area ratio of the zinc indicates a small mass of the zinc in contact with the body fluid per unit time, a low release rate of zinc in the zinc-containing layer, and a low generation rate of zinc-containing substances. The high mass-to-surface area ratio of the zinc indicates a large mass of the zinc in contact with the body fluid per unit time, a high release rate of zinc in the zinc-containing layer, and a high generation rate of zinc-containing substances.

The average porosity of a bulk material refers to a ratio of a pore volume in a bulk material to a total volume of the bulk material in a natural state. The average porosity of the bulk material reflects the compaction of the material. Accordingly, for the zinc-containing layer of the implantable device described above, when the average porosity of the zinc-containing layer is larger, the zinc-containing layer is more porous, and the release rate of the zinc is higher. A small average porosity indicates that the zinc-containing layer is dense, and the release rate of zinc is low.

When the mass-to-surface area ratio of the zinc in the zinc-containing layer is 0.1-200 µg/mm² and the average porosity of the zinc-containing layer is less than or equal to 30%, the mass-to-surface area ratio of the zinc elements in the zinc-containing layer is matched with the average porosity of the zinc-containing layer, so that the release rate of the zinc can be controlled within a reasonable range, and the generation rate of zinc-containing substances can be controlled. Therefore, the concentration of the zinc-containing substances in the tissues around the implantable device can inhibit the proliferation of the smooth muscle cells, meanwhile, the peak concentration of the zinc-containing substances at the highest concentration is ensured not to cause the death of smooth muscle cells, endothelial cells and other normal tissue cells, and the ulceration or necrosis of the tissues around the implantable device is avoided.

In an exemplary embodiment, when the mass-to-surface area ratio of the zinc in the zinc-containing layer is high, the average porosity of the zinc-containing layer may need to be reduced; and when the mass-to-surface area ratio of the zinc in the zinc-containing layer is low, the average porosity of the zinc-containing layer may need to be increased, so that the mass-to-surface area and the average porosity are well matched.

In an exemplary embodiment, the mass-to-surface area ratio of the zinc in the zinc-containing layer is 1 to 150 µg/mm², and the porosity of the zinc-containing layer is 0 to 10%, to ensure that the zinc-containing substances have a longer release time without causing the cell death in normal tissues, and to ensure that the tissues around the implantable device do not develop severe hyperplasia in one to three months.

In a further embodiment, the mass-to-surface area ratio of the zinc in the zinc-containing layer is 50 to 100 µg/mm², and the porosity of the zinc-containing layer is 5% to 10%. The mass-to-surface area ratio of the zinc and the porosity of the zinc-containing layer are selected to be well matched, so that neither severe hyperplasia and tissue ulceration nor necrosis of the tissues around the implantable device occur in the repairing period of the lesion.

It may be contemplated that the pores in the above zinc-containing layer refer to the pores in the material constituting the zinc-containing layer, not including holes, pores or crevices added to the surface or inside of the zinc-containing layer due to the irregular, discontinuous or uneven distribution of the zinc-containing layer.

In an embodiment, the zinc-containing layer further includes a polymer. The zinc compound is dispersed in the polymer.

The polymer is selected from at least one of degradable polymer and non-degradable polymer. The degradable polymer is selected from at least one of polylactic acid, polyglycolic acid, polycaprolactone, polyethylene succinate, polybutylene succinate and poly(β-hydroxybutyrate), and the non-degradable polymer is selected from polystyrene, polytetrafluoroethylene, polymethyl methacrylate, polycarbonate or polyethylene terephthalate.

In a further exemplary implementation mode, the polymer is selected from at least one of copolymers formed by at least one monomer forming the degradable polymers and at least one monomer forming the non-degradable polymers.

When the zinc compound contained in the zinc-containing layer is a water-soluble compound, the zinc-containing layer is easy to release after contacting the body fluid, and the zinc-containing layer contains the polymer, so that the release rate of the zinc compound can be adjusted, and the zinc compound is prevented from being released too quickly. In an embodiment, a mass ratio of the zinc compound to polymer ranges from 7:200 to 5:4.

It may be contemplated that when the zinc-containing layer is multilayer, any one of the zinc-containing layers may contain at least one polymer or none of the layers may contain the polymer.

In a further embodiment, a weight average molecular weight of the above polymer is 100,000 to 500,000. The weight average molecular weight of the polymer is larger, the dissolution or degradation rate of the polymer is lower, and the release rate of the zinc-containing substances is lower; and otherwise, the weight average molecular weight of the polymer is smaller, the dissolution or degradation rate of the polymer is higher, and the release rate of the zinc-containing substances is higher. When the weight average molecular weight of the polymer ranges from 100,000 to 500,000, the dissolution or degradation rate of the polymer is moderate, and the release of the zinc-containing substances may last for one to three months.

In an exemplary embodiment, the content of zinc elements in the zinc-containing layer is 1.4 wt. % to 80 wt. %. When the release rate of the zinc-containing substances is basically constant, the zinc content of the zinc-containing layer is higher, the total mass of the zinc-containing substances is larger, and therefore the release time of the zinc-containing substances is longer. When the zinc content is lower, the total mass of the zinc-containing substances is smaller, and the release time of the zinc-containing substance is shorter. The content of the zinc elements in the zinc-containing layer is set in a range of 1.4 wt. % to 80 wt. %, so that the effective release time of the zinc-containing substances can last for one to three months without affecting the normal endothelialization of the implantable device.

It can be understood that when the zinc-containing layer contains the zinc compound and the polymer, the content of the zinc elements is 1.4 wt. % to 80 wt. %, which refers to that the percentage of the mass of the zinc elements in the sum of the mass of the zinc-containing compound and polymer is 1.4 wt. % to 80 wt. %. When the zinc-containing layer only contains the zinc compound, the content of the zinc elements is 1.4 wt. % to 80 wt. %, which refers to the mass percentage of the zinc elements in the zinc compound.

In an exemplary embodiment, a thickness of the zinc-containing layer is 1 µm to 50 µm. The thickness of the zinc-containing layer may affect the length of time that the zinc-containing substances are maintained in the tissues around the zinc-containing layer at an effective concentration of inhibiting the proliferation without killing the normal tissue cells. When the thickness of the zinc-containing layer ranges from 1 µm to 50 µm, the zinc-containing substances can be maintained in the tissues around the zinc-containing layer at the effective concentration of inhibiting the proliferation of the smooth muscle cells without killing the normal tissue cells for one to three months.

In a further embodiment, the thickness of the zinc-containing layer is 20 µm to 30 µm.

It may be contemplated that when the number of layers of the zinc-containing layer is one, the thickness of the zinc-containing layer is 1 µm to 50 µm, and may be 20 µm to 30 µm; and when the number of layers of the zinc-containing layer is multiple, the sum of the thicknesses of the zinc-containing layers is 1 µm to 50 µm, and the sum of the thicknesses of the zinc-containing layers may be 20 µm to 30 µm.

In an exemplary implementation mode, the implantable device further includes a barrier layer. The barrier layer at least partially covers the zinc-containing layer.

The barrier layer contains a polymer. The polymer is selected from at least one of degradable polymer and non-degradable polymer. In a further implementation mode, the polymer is selected from at least one of copolymers formed by at least one monomer forming the degradable polymer and at least one monomer forming the non-degradable polymer. The degradable polymer is selected from at least one of polylactic acid, polyglycolic acid, polycaprolactone, polyethylene succinate, polybutylene succinate and poly(β-hydroxybutyrate), and the non-degradable polyester is selected from at least one of polystyrene, polytetrafluoroethylene, polymethyl methacrylate, polycarbonate or polyethylene terephthalate.

When the zinc compound contained in the zinc-containing layer is a water-soluble compound, the zinc-containing layer is easy to release after contacting the body fluid, and the zinc-containing layer is partially covered by the barrier layer, so that the release rate of the zinc compound can be adjusted, and the zinc compound is prevented from being released too quickly.

In an exemplary embodiment, a sum of the thicknesses of the zinc-containing layer and barrier layer is less than or equal to 50 μm. A ratio of the thickness of the zinc-containing layer to the thickness of the barrier layer is 1:9 to 9:1.

It may be contemplated that the zinc-containing layer at least partially covered by the barrier layer may be a zinc-containing layer only containing the zinc compound, and may also be a zinc-containing layer containing both the zinc compound and the polymer, and the release of the zinc-containing substances can be well adjusted by reasonably adjusting the ratio of the zinc compound to the polymer and controlling the thickness of the barrier layer.

It may be contemplated that in the implementation mode that the zinc-containing layer is multilayer, the barrier layer may partially cover the zinc-containing layer on the outermost layer, i.e. partially cover the zinc-containing layer furthest from the substrate.

It may be contemplated that neither the polymer in the zinc-containing layer nor the polymer in the barrier layer is limited to the polymers described above, and any polymer which is non-toxic and harmless to the human body, capable of limiting the release rate of the soluble zinc compound, and capable of being mixed with the zinc compound and forming a coating or capable of forming a coating on the zinc-containing layer can be used in the implantable device described above.

By reasonably controlling the mass-to-surface area ratio of the zinc in the zinc-containing layer to be 0.1 to 200 μg/mm$^2$ and the average porosity of the zinc-containing layer to be less than or equal to 30%, the zinc compound in the zinc-containing layer is released and corroded or dissolved to generate zinc-containing substances after the implantable device is implanted in the body, and the concentration of the zinc-containing substances in the tissues around the implantable device is controlled by controlling the release rate of the zinc-containing substances, so that not only can the proliferation of the smooth muscle cells of the tissues around the device be effectively inhibited, but also the ulceration or necrosis of the tissues around the device caused by the fact that the concentration of zinc-containing substances accumulated in the tissues is greater than the cytotoxic concentration after the implantable device is implanted can be avoided, and the safety is greatly improved.

The implantable device may be a vascular stent, a biliary stent, an esophageal stent, a urethral stent, an airway stent, or a vena cava filter.

An exemplary implantable device is prepared by first preparing a substrate according to a method mastered by those skilled in the art, for example, the lumen vascular stent 10 of FIG. 1 can be made by making a lumen vascular stent preform in a pulling way, forming stent patterns by cutting to obtain a lumen stent substrate and then forming a zinc-containing layer and a barrier layer on the lumen vascular stent substrate by a method mastered by those skilled in the art, such as plasma spraying, ultrasonic atomization spraying and the like.

The implantable device is further described below with reference to the figures and embodiments.

In the following embodiments, the following detection methods are used:

1. Detecting a mass-to-surface area ratio of zinc of the implantable device:

A detection method of the mass-to-surface area ratio of the zinc includes the following steps: strong acid or strong alkali is used to dissolve the implantable device, and distilled water is added to obtain a uniform solution with a constant volume of V. Then the zinc concentration ($C_{zinc}$) in the uniform solution is detected by an atomic absorption spectrum method, wherein the mass the zinc elements in the zinc-containing layer ($M_{zinc}$) is equal to $C_{zinc} \times V$. Calipers, microscopes, or other image measuring devices are used to measure the surface area ($S_{device}$) of the implantable device, and the mass-to-surface area ratio of the zinc in the implantable device is then $M_{zinc}/S_{device}$.

Exemplary conditions of the atomic absorption spectrum are as follows:

Agilent Spectr AA 240FS atomic absorption spectrometer;

Detection wavelength: 213.9 nm; slit: 1.0 nm; light source: Agilent zinc hollow cathode lamp; current: 5.0 mA; automatic gain 44%;

Furnace body height: 0 mm; flow rate of acetylene combustion-supporting gas: 2.00 L/min; flow rate of compressed air: 13.50 L/min; acetylene gas pressure: 75 kPa; compressed air pressure: 0.4 MPa; deuterium lamp buckle background: on; measurement time: 5 seconds; pre-reading delay: 10 seconds; reading times: three times; standard curve fitting: linearity.

2. Detecting an average porosity of the zinc-containing layer of the implantable device:

The average porosity of the zinc-containing layer is detected according to GB/T 15749-2008: *Measuring method in quantitative metallography* which may include the following steps: the implantable device is frozen for 1 to 10 min in liquid nitrogen to improve the fragility of a sample. The sample is taken out and rapidly broken, and a fractured section of the sample is coated with a conductive layer (for example, gold, silver). The position of the zinc-containing layer in the section is determined by an accessory, an energy dispersive spectrometer, of a scanning electron microscope (SEM) (the influence of the barrier layer may be ignored after the position of the zinc-containing layer is determined), and then the zinc-containing layer on the section is observed through the SEM. At least 10 fields of view are randomly selected, grids are respectively drawn to cover an SEM picture taken at each field of view, and a proportion of all pores in the total area of the field of view is calculated through the number of grid points occupied by all pores in the field of view or a length of a cut grid line segment. At least three sections of a portion of the implantable device having the zinc-containing layer are repeatedly selected, at least 10 fields of view are randomly selected in each section, and the ratio of all measured pores in each field of view to the total area of the field of view is averaged, i.e. taken as the average porosity of the zinc-containing layer of the implantable device.

Wherein, in an exemplary embodiment, XPS is an ESCALAB 250Xi X-ray photoelectron spectrometer from Thermo Fisher Corporation, and SEM is a JSM6510 scanning electron microscope from JEOL.

3. Detecting a zinc content in the zinc-containing layer of the implantable device:

The zinc content of the zinc-containing layer is detected by the X-ray photoelectron spectroscope (XPS) or SEM, which may include the following steps: the portion of the implantable device having the zinc-containing layer is embedded and fixed by a resin, and is ground and polished on a metallographic sample pre-milling machine, and then a cross-section of the zinc-containing layer of the implantable device is observed through XPS or SEM. At least three sections of the zinc-containing layer of the implantable device are selected, a square area with the same area is selected in each section, and the zinc content of the square area is detected by an accessory of XPS or SEM—the energy dispersive spectrometer. The zinc content of the square area of each section is summed up and then averaged, thus obtaining the zinc content of the zinc-containing layer.

Wherein, in an exemplary embodiment, XPS is an ESCALAB 250Xi X-ray photoelectron spectrometer from Thermo Fisher Corporation, and SEM is a JSM6510 scanning electron microscope from JEOL.

4. Detecting a thickness of the zinc-containing layer of the implantable device:

The thickness of the zinc-containing layer is detected by the following method: the portion of the implantable device having the zinc-containing layer is embedded and fixed by a resin and is ground and polished on a metallographic sample pre-milling machine until a cross section of the implantable device having the zinc-containing layer is exposed. At least three sections perpendicular to the surface of the device are selected and then observed through SEM. The position of the zinc-containing layer in the cross section is determined by the accessory of SEM—the energy dispersive spectrometer, and the thickness of at least three positions of the zinc-containing layer along a normal direction of the surface of the implantable device is detected. The thicknesses of the zinc-containing layer at the positions are summed up and then averaged, thus obtaining the thickness of the zinc-containing layer. In order to observe the thickness of the barrier layer, a conductive layer (for example, gold, and silver) is sprayed on the surface of the device before the device is embedded with the resin, the position of the barrier layer is determined through the energy dispersive spectrometer, and the method for detecting the thickness refers to the detection of the thickness of the zinc-containing layer.

Wherein, in an exemplary embodiment, XPS is an ESCALAB 250Xi X-ray photoelectron spectrometer from Thermo Fisher Corporation, and SEM is a JSM6510 scanning electron microscope from JEOL.

5. Detection method for a weight average molecular weight of the polymer:

The weight average molecular weight of the polymer is detected by a GPC-multi-angle laser light scattering instrument of American Wyatt Company in combination with a molecular weight test system. The test system includes a liquid phase pump and a sample injector from American Agilent Company, a Agilent PL MIXED-C GPC column from American Agilent Company (dimensions: 7.5×300 mm, 5 micrometers), a multi-angle laser light scattering instrument from American Wyatt Company and a differential detector from American Wyatt Company. Detection conditions: mobile phase: tetrahydrofuran; flow rate of the pump: 1 mL/mi; sample feed quantity: 100 μL; laser wavelength: 663.9 nm; test temperature: 35° C.

6. Detecting a stenosis rate in tissues around the implantable device:

The stenosis rate in the tissues around the implantable device is detected through animal implantation tests in combination with optical coherence tomography (OCT).

When the implantable device is a vascular stent, the effect of zinc corrosion products in inhibiting proliferation is evaluated by using the lumen stenosis rate as a reference index. The lumen stenosis rate can be obtained by measuring the blood vessel lumen around the vascular stent by using the OCT and performing calculation according to the following calculation formula:

$$\text{Lumen stenosis rate} = (\text{original lumen area} - \text{existing lumen area})/\text{original lumen area} \times 100\%.$$

It may be contemplated that the lumen stenosis rate reflects the stenosis of a lumen. The low stenosis rate of lumen indicates that the effect in inhibiting the proliferation is good; and the high lumen stenosis rate indicates that the effect in inhibiting proliferation is poor.

The vascular stent is taken as an example, and the following exemplary steps may be included: the vascular stent is implanted into a blood vessel of a test animal. Then, at a predetermined observation time (for example, one month, three months and six months), the vascular stent and vascular tissues around the vascular stent are taken out. The original lumen area and the existing lumen area of the blood vessels around the vascular stent are respectively measured by a vascular optical interference tomography system from American LightLab Imaging Company, and the lumen stenosis rate=(original lumen area−existing lumen area)/original lumen area×100%.

In a first exemplary embodiment, the surface of a pure iron stent substrate may be uniformly sprayed with a layer of zinc oxide using APS-2000 plasma spraying equipment in a plasma spraying mode, and a zinc-containing layer may be formed on the surface of the pure iron stent substrate, and thus obtaining the vascular stent of the present embodiment. The technological conditions of the plasma spraying may be as follows: a main gas may be argon, a flow rate of the argon may be 40 L/min, an arc current may be 500 A, the arc voltage may be 50 V, a spraying distance may be 100 mm, and a flow rate of the powder feeding gas may be 0.4 L/min.

By the above-mentioned detection method, the vascular stent provided by a first exemplary embodiment 1 may have a mass-to-surface area ratio of the zinc of 150 μg/mm$^2$, an average porosity of the zinc-containing layer of 3%, a zinc content in the zinc-containing layer of 80 wt. %, and a thickness of the zinc-containing layer of 32 μm.

Figure 2:
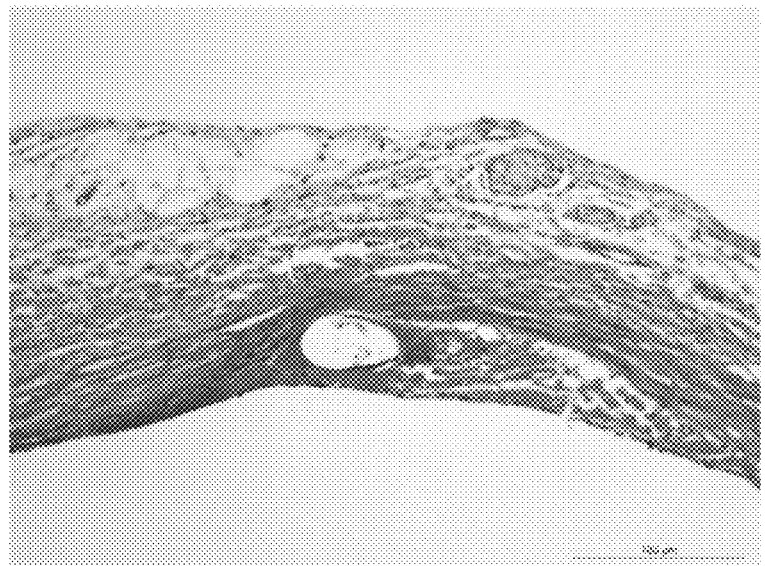
FIG. 2 is a pathological section of tissues around the vascular stent one month after an exemplary vascular stent is implanted into a coronary vessel of a minipig.

The vascular stent of embodiment 1 may be implanted into a coronary vessel of a minipig, and an over-expansion ratio may be kept in a range of 1.1:1 to 1.2:1 during the implantation. By virtue of follow-up after the device is implanted for one month, it could be known from the OCT measurement data that the stenosis rate of the blood vessels around the stent may be 8%, the tissues around the stent are subjected to pathological analysis, and a pathological picture may be shown in FIG. 2. The pathological analysis results may show that the vascular stent provided by the embodiment 1 could effectively inhibit the proliferation of the smooth muscle cells of the vascular tissues around the stent after being implanted into the animal body for 1 month, no tissue cell necrosis existed around stent struts, and endothelial cells of the vascular tissues grew normally.

Embodiment 2

Zinc lactate and polylactic acid in a mass ratio of 3:44 may be mixed and then dissolved in a mixed solvent of medical-grade ethyl acetate and absolute ethanol in a volume ratio of 20:1 to prepare a mixed solution in which a zinc lactate concentration may be 0.3 mg/mL and a polylactic acid concentration may be 4.4 mg/mL, and the obtained mixture may be sprayed on the surface of a pure iron stent substrate in an ultrasonic atomization spraying mode to form a zinc-containing layer on the surface of the pure iron stent substrate, thus obtaining the vascular stent of the present embodiment. The spraying equipment may be MediCoat DES4000 equipment. The pumping rate of the equipment may be 0.05 mL/min, the ultrasonic intensity may be 70%, the rotation speed may be 250 r/min, the advancing speed may be 0.3 cm/s, and the stroke may be four times.

By the above-mentioned detection method, the vascular stent provided by embodiment 2 may have a mass-to-surface area ratio of the zinc of 1 μg/mm$^2$, an average porosity of the zinc-containing layer of 8%, a zinc content in the zinc-containing layer of 1.4 wt. %, a thickness of the zinc-containing layer of 10 μm, and a weight average molecular weight of the polylactic acid of 500,000.

Figure 3:
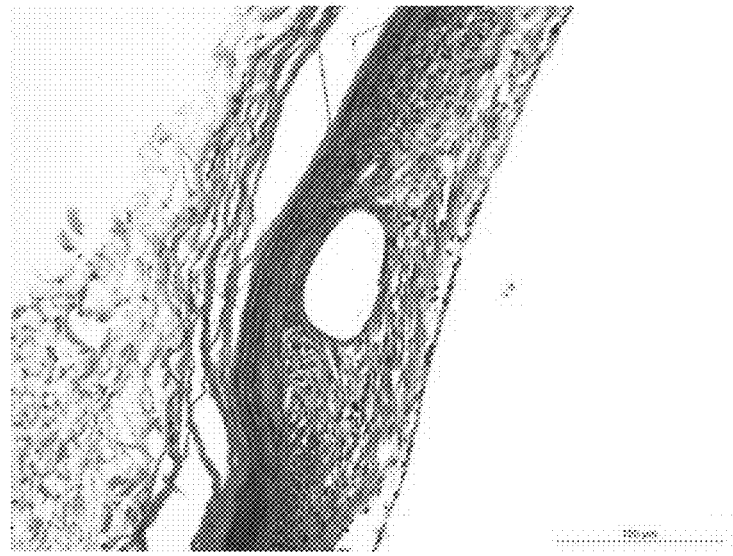
FIG. 3 is a pathological section of tissues around the vascular stent one month after an exemplary vascular stent is implanted into the coronary vessel of the minipig.

The vascular stent of the present embodiment may be implanted into a coronary vessel of a minipig, and an over-expansion ratio may be kept in a range of 1.1:1 to 1.2:1 during the implantation. After the device is implanted for one month, it could be known from the OCT measurement data that the stenosis rate of the blood vessels around the stent may be 10%, the stent and the vascular tissues around the stent are taken out for pathological analysis, and a pathological picture may be shown in FIG. 3. The pathological analysis results may show that after the vascular stent provided by the embodiment 2 has been implanted in the animal body for one month, there may be no obvious smooth muscle cell proliferation in the tissue around the stent, and no tissue cell necrosis existed around the stent struts.

Embodiment 3

Zinc gluconate and polylactic acid in a mass ratio of 4:11 may be mixed and then dissolved in a mixed solvent of medical-grade ethyl acetate and absolute ethanol in a volume ratio of 20:1 to prepare a mixed solution in which a zinc gluconate concentration may be 0.4 mg/mL and a polylactic acid concentration may be 1.1 mg/mL, then the obtained mixture may be sprayed on the surface of a conventional 304 stainless steel vascular stent substrate by using MediCoat DES4000 equipment in an ultrasonic atomization spraying mode to form a zinc-containing layer on the surface of the vascular stent substrate; and then a layer of polylactic acid barrier layer (5 mg/ml, polylactic acid ethyl acetate solution) is formed on the zinc-containing layer by an ultrasonic atomization spraying method, thus obtaining the vascular stent. When sprayed to form the zinc-containing layer, the pumping rate of the equipment may be 0.08 mL/min, the ultrasonic intensity may be 70%, the rotation speed may be 250 r/min, the advancing speed may be 0.1 cm/s, and the stroke may be two times; and when sprayed to form the barrier layer, the pumping rate may be 0.04 mL/min, the ultrasonic intensity may be 50%, the rotation speed may be 250 r/min, the advancing speed may be 0.1 cm/s, and the stroke may be two times.

By the above-mentioned detection method, the vascular stent provided by embodiment 3 may have a mass-to-surface area ratio of the zinc of 2 μg/mm$^2$, an average porosity of the zinc-containing layer of 15%, the zinc content in the zinc-containing layer of 8 wt. %, a thickness of the zinc-containing layer of 37 μm, a thickness of the barrier layer of 11 μm, and a weight average molecular weight of the polylactic acid of 200,000.

The vascular stent of the present embodiment may be implanted into a coronary vessel of a minipig. An over-expansion ratio may be kept in a range of 1.1:1 to 1.2:1 during the implantation. After the device is implanted for one month, it could be known from the OCT measurement data that the stenosis rate of the blood vessels around the stent may be 15%, and the stent and the vascular tissues around the stent are taken out for pathological analysis. The pathological analysis results may show may show that the vascular stent provided by the embodiment 3 may inhibit proliferation of the smooth muscle cells of the vascular tissues to a certain extent after being implanted into the animal body for 1 month, no tissue cell necrosis exists around stent struts, and endothelial cells of the vascular tissues may also grow normally.

Embodiment 4

Figure 4:
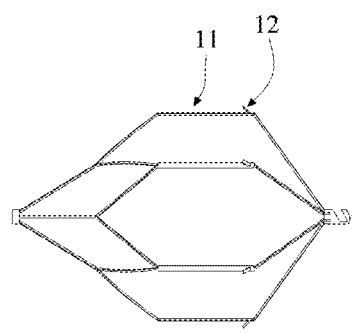
FIG. 4 is a schematic structural diagram of an exemplary vena cava filter.

FIG. 4 shows a vena cava filter made of a nickel-titanium alloy material. A substrate of the vena cava filter consists of a number of supporting rods 11, and one end of each supporting rod 11 is provided with a fixed anchor 12. After the vena cava filter is implanted, the fixed anchors 12 penetrate inner walls of the blood vessels to fix the vena cava filter. All supporting rods 11 and fixed anchors 12 are sprayed with a layer of zinc sulfide and zinc oxide mixture in a plasma spraying mode, and a mass ratio of the zinc sulfide to the zinc oxide is 12:25, and the zinc-containing layer is coated with a layer of polycaprolactone (5 mg/mL, polyglycolide ethyl acetate solution) by MediCoat DES4000 equipment, thus obtaining the vena cava filter of the present embodiment. The technological conditions of plasma spraying are as follows: a main gas is argon, a flow rate of the argon is 40 L/min, an arc current is 500 A, an arc voltage is 50 V, a spraying distance is 100 mm, and a powder feeding gas flow rate is 0.4 L/min; and the spraying equipment is MediCoat DES4000 equipment, the pumping rate is 0.05 mL/min, the ultrasonic intensity is 60%, the rotation speed is 250 r/min, the advancing speed is 0.1 cm/s, and the stroke is two times.

By the above-mentioned detection method, the vena cava filter provided by embodiment 4 may have a mass-to-surface area ratio of the zinc of 5 μg/mm$^2$, the average porosity of the zinc-containing layer of 10%, the zinc content in the zinc-containing layer of 76 wt. %, the thickness of the zinc-containing layer of 24 μm, the thickness of the barrier layer of 16 μm, and the weight average molecular weight of the polycaprolactone of 100,000.

The vena cava filter provided by embodiment 4 may be implanted into inferior vena cava of a dog. After the vena cava filter is implanted for one month, the filter and the vascular tissues around the filter may be taken out, the vascular tissues around the fixed anchors of the vena cava filter may be separated, and paraffin-embedded tissue sections of the vascular tissues may be prepared for pathological analysis.

The pathological analysis results may show that after the vena cava filter provided by embodiment 4 is implanted for one month, there may be no obvious proliferation of the smooth muscle cells of the vascular tissues around the fixed anchors.

Embodiment 5

The surface of the vascular stent substrate made of an iron-magnesium alloy material may be sprayed with a layer of zinc sulfide in a plasma spraying mode to form a zinc-containing layer, thus obtaining the vascular stent of the present embodiment. The technological conditions of the plasma spraying may be as follows: a main gas may be argon, a flow rate of argon may be 31 L/min, an arc current may be 485 A, an arc voltage may be 50 V, a spraying distance may be 150 mm, and a flow rate of the powder feeding gas may be 0.2 L/min By the above-mentioned detection method, the vascular stent provided by embodiment 5 may have a mass-to-surface area ratio of the zinc of 0.1 µg/mm$^2$, an average porosity of the zinc-containing layer of 30%, a zinc content in the zinc-containing layer of 67 wt. %, and a thickness of the zinc-containing layer of 1 µm.

Figure 5:
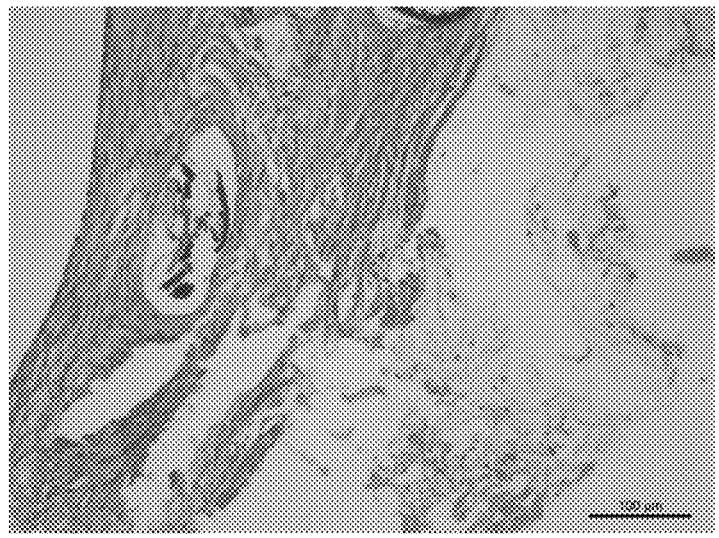
FIG. 5 is a pathological section of tissues around the vascular stent one month after an exemplary vascular stent is implanted into the coronary vessel of the minipig.

The vascular stent provided by embodiment 5 may be implanted into a coronary vessel of a minipig, and an over-expansion ratio may be kept in a range of 1.1:1 to 1.2:1 during the implantation. After the device is implanted for one month, it could be known from the OCT measurement data that the stenosis rate of the blood vessels around the stent may be 20%, the stent and the vascular tissues around the stent are taken out for pathological analysis, and a pathological picture may be shown in FIG. 5. The pathological analysis results may show that after the vascular stent provided by the embodiment 5 has been implanted for one month, there may be no obvious proliferation of the smooth muscle cells of the vascular tissues around the stent, and no tissue cell necrosis existed around the stent struts.

Embodiment 6

The surface of the vascular stent substrate made of an iron-magnesium alloy material may be sprayed with a layer of zinc sulfide in a plasma spraying mode, and then the surface of the zinc sulfide may be uniformly coated with a layer of zinc lactate and polystyrene mixture (the zinc lactate concentration may be 0.3 mg/mL, and the polystyrene concentration may be 4.4 mg/mL) through the MediCoat DES4000 equipment to form a zinc-containing layer with the zinc sulfide layer. The surface of the zinc-containing layer may be further uniformly coated with a layer of polylactic acid (5 mg/mL, polylactic acid ethyl acetate solution) through the MediCoat DES4000 equipment, and a barrier layer may be formed. The technological conditions of plasma spraying may be as follows: a main gas may be argon, a flow rate of the argon may be 38 L/min, an arc current may be 485 A, an arc voltage may be 50 V, a spraying distance may be 120 mm, and a powder feeding gas flow rate may be 0.38 L/min; when sprayed to form the zinc-containing layer, the pumping rate of the equipment may be 0.05 mL/min, the ultrasonic intensity may be 50%, the rotation speed may be 250 r/min, the advancing speed may be 0.1 cm/s, and the stroke may be two times; and when sprayed to form the barrier layer was, the pumping rate may be 0.04 mL/min, the ultrasonic intensity may be 50%, the rotation speed may be 270 r/min, the advancing speed may be 0.1 cm/s, and the stroke may be one time.

By the above-mentioned detection method, the vascular stent provided by embodiment 6 may have a mass-to-surface area ratio of the zinc of 50 µg/mm$^2$, the average porosity of the zinc-containing layer of 10%, the zinc content in the zinc-containing layer of 67 wt. %, the thickness of the zinc-containing layer of 25 µm (a sum of thicknesses of the zinc sulfide layer and the zinc-containing layer formed by the zinc lactate and polystyrene), the thickness of the barrier layer may be 5 µm, and the weight average molecular weight of the polylactic acid may be 200,000.

Figure 6:
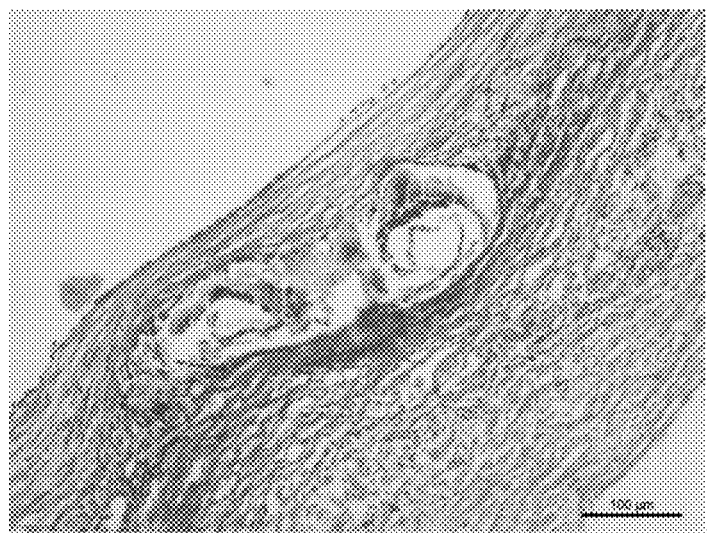
FIG. 6 is a pathological section of tissues around the vascular stent two months after an exemplary vascular stent is implanted into the coronary vessel of the minipig.

The vascular stent provided by embodiment 6 may be implanted into a coronary vessel of a minipig, and an over-expansion ratio may be kept in a range of 1.1:1 to 1.2:1 during the implantation. After the device is implanted for two months, it could be known from the OCT measurement data that the stenosis rate of the blood vessels around the stent may be 10%, the stent and the vascular tissues around the stent may be taken out for pathological analysis, and a pathological picture may be shown in FIG. 6. The pathological analysis results may show that after the vascular stent provided by the embodiment 6 has been implanted for two months, there may be no obvious proliferation of the smooth muscle cells of the vascular tissues around the stent, and no tissue cell necrosis may exist around the stent struts.

Embodiment 7

The surface of the pure iron stent substrate may be coated with a layer of zinc phosphate and zinc oxide in a high-speed cold spraying mode, and a ratio of the zinc phosphate to zinc oxide may be 1.43:1. Before the spraying, zinc phosphate and zinc oxide solids may be mixed and processed by a grinding machine to obtain powder with a granularity of 5 µm to 15 µm. A spray nozzle of the equipment adopted a De-Laval model with a diameter of 2 mm. The working gas may be He, the gas pressure may be 2 MPa, the gas speed may be 2 m$^3$/min, the gas temperature may be 600° C., the spraying distance may be 40 mm, and the powder feeding speed may be 10 kg/h. After the spraying, a zinc-containing layer may be formed on the pure iron stent substrate, thus obtaining the vascular stent of embodiment 7.

By the above-mentioned detection method, the vascular stent provided by exemplary embodiment 7 may be measured to have a mass-to-surface area ratio of the zinc of 200 µg/mm$^2$, an average porosity of the zinc-containing layer of 1%, a zinc content in the zinc-containing layer of 43 wt. %, and a thickness of the zinc-containing layer of 50 µm.

Figure 7:
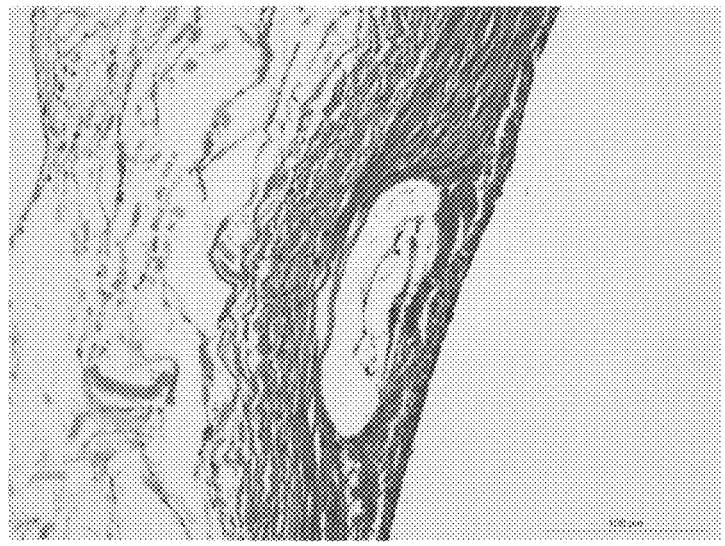
FIG. 7 is a pathological section of tissues around the vascular stent one month after an exemplary vascular stent is implanted into the coronary vessel of the minipig.

The vascular stent provided by embodiment 7 may be implanted into a coronary vessel of a minipig, and an over-expansion ratio may be kept in a range of 1.1:1 to 1.2:1 during the implantation. After the device is implanted for one month, the stent and the vascular tissues around the stent may be taken out for pathological analysis, and a pathological picture may be shown in FIG. 7. The pathological analysis results may show that after the vascular stent provided by the embodiment 7 has been implanted for one month, there may be no obvious proliferation of the smooth muscle cells of the vascular tissues around the stent, and no tissue cell necrosis existed around the stent struts.

Embodiment 8

The zinc phosphate solid may be processed by a grinding machine to obtain zinc phosphate powder having a particle size ranging from 5 μm to 20 μm. The surface of a pure iron stent substrate may be uniformly sprayed with a layer of zinc phosphate in a high-speed cold spraying mode, and a zinc-containing layer may be formed on the pure iron stent substrate, thus obtaining the vascular stent of embodiment 8. A spray nozzle of the equipment adopted a De-Laval model with a diameter of 2 mm. The working gas may be He, the gas pressure may be 1.5 MPa, the gas speed may be 2 m$^3$/min, the gas temperature may be 1000° C., the spraying distance may be 40 mm, and the powder feeding speed may be 10 kg/h.

By the above-mentioned detection method, the vascular stent provided by embodiment 8 may be measured to have a mass-to-surface area ratio of the zinc of 100 μg/mm$^2$, an average porosity of the zinc-containing layer of 5%, a zinc content in the zinc-containing layer of 17 wt. %, and a thickness of the zinc-containing layer of 50 μm.

The vascular stent provided by embodiment 8 may be implanted into a coronary vessel of a minipig, and an over-expansion ratio may be kept in a range of 1.1:1 to 1.2:1 during the implantation. After the device is implanted for one month, the stent and the vascular tissues around the stent may be taken out for pathological analysis. The pathological analysis results may show that after the vascular stent provided by the embodiment 8 has been implanted for 3 months, there may be no obvious proliferation of the smooth muscle cells of the vascular tissues around the stent, and no tissue cell necrosis existed around the stent struts.

Embodiment 9

The zinc gluconate solid may be processed by a grinding machine to obtain zinc gluconate powder having a particle size less than 5 μm. The zinc gluconate powder and polylactic acid in a mass ratio of 10:3 may be mixed and then dissolved in ethyl acetate, the concentration of the zinc gluconate may be 14 mg/mL, the concentration of the polylactic acid may be 4.2 mg/mL, then the obtained mixture may be sprayed on the surface of the stent substrate made of the iron-magnesium alloy material through the MediCoat DES4000 equipment to form a zinc-containing layer, thus obtaining the vascular stent of the present embodiment. The pumping rate of the spraying equipment may be 0.07 mL/min, the ultrasonic intensity may be 50%, the rotation speed may be 250 r/min, the advancing speed may be 0.2 cm/s, and the stroke may be four times.

By the above-mentioned detection method, the vascular stent provided by embodiment 9 may be measured to have a mass-to-surface area ratio of the zinc of 10 μg/mm$^2$, an average porosity of the zinc-containing layer of 10%, a zinc content in the zinc-containing layer of 50 wt. %, a thickness of the zinc-containing layer of 25 μm, and a weight average molecular weight of the polylactic acid of 200,000.

The vascular stent provided by embodiment 9 may be implanted into a coronary vessel of a minipig, and an over-expansion ratio may be kept in a range of 1.1:1 to 1.2:1 during the implantation. After the device has been implanted for 3 months, the OCT measurement data may indicate that the stenosis rate of the blood vessels around the stent is approximately 15%, and the stent and the vascular tissues around the stent may be taken out for pathological analysis. The pathological analysis results may show that after the vascular stent provided by the embodiment 9 has been implanted for 3 months, there may be no obvious proliferation of the smooth muscle cells of the vascular tissues around the vascular stent, and no tissue cell necrosis existed around the stent struts.

COMPARATIVE EXAMPLE 1

The surface of a pure iron stent substrate may be uniformly sprayed with a layer of zinc oxide using APS-2000 plasma spraying equipment in a plasma spraying mode, and a zinc-containing layer may be formed on the pure iron stent substrate, thus obtaining the vascular stent of the comparative example 1. The technological conditions of an exemplary plasma spraying may be as follows: a main gas may be argon, a flow rate of the argon may be 23 L/min, an arc current may be 500 A, an arc voltage may be 50 V, a spraying distance may be 120 mm, and a flow rate of the powder feeding gas may be 0.4 L/min.

By the above-mentioned detection method, the vascular stent provided by the comparative example 1 may be measured to have a mass-to-surface area ratio of the zinc of 150 μg/mm$^2$, an average porosity of the zinc-containing layer of 40%, a zinc content in the zinc-containing layer of 80 wt. %, and a thickness of the zinc-containing layer of 32 μm.

Figure 8:
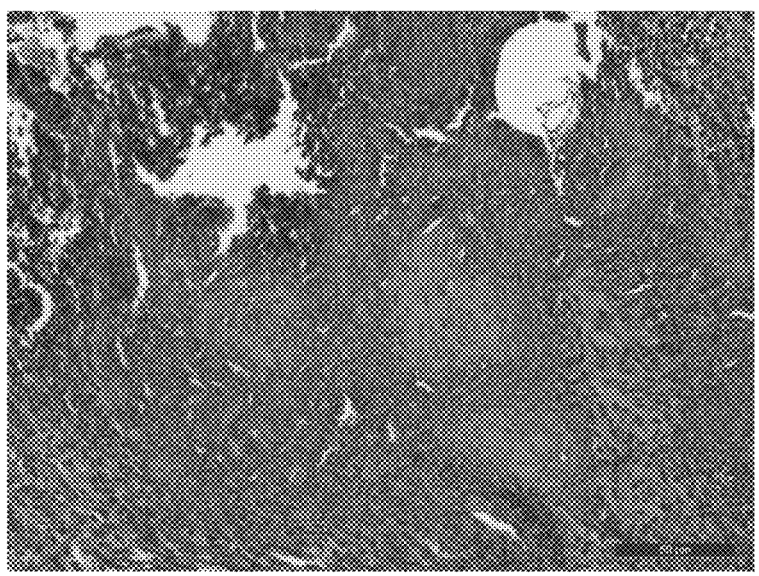
FIG. 8 is a pathological section of tissues around the vascular stent one month after an exemplary vascular stent is implanted into the coronary vessel of a minipig.

The vascular stent of the comparative example 1 may be implanted into a coronary vessel of a minipig, and an over-expansion ratio may be kept in a range of 1.1:1 to 1.2:1 during the implantation. By virtue of follow-up after the device is implanted for one month, it could be known from the OCT measurement data that the stenosis rate of the blood vessels around the stent may be 5%, pathological analysis may be carried out on the tissues around the stent, and a pathological picture may be shown in FIG. 8. The pathological analysis results may show that after the vascular stent provided by the comparative example 1 has been implanted for 1 month, the proliferation of the smooth muscle cells of the vascular tissues around the stent could be effectively inhibited, but the tissue cell necrosis may be presented.

The result indicates that compared with embodiment 1, in the vascular stent of the comparative example 1, the average porosity of the zinc-containing layer is higher, resulting in excessively higher generation rate of the zinc-containing substances in the tissues around the stent, and excessively high concentration of the zinc-containing substances accumulated in the tissues, which causes the tissue cell necrosis.

COMPARATIVE EXAMPLE 2

Zinc lactate and polylactic acid in a mass ratio of 3:44 may be mixed and then dissolved in a mixed solvent of ethyl acetate and ethyl alcohol in a volume ratio of 20:1 to prepare a mixed solution in which a zinc lactate concentration may be 0.3 mg/mL and a polylactic acid concentration may be 4.4 mg/mL, and the obtained mixture may be sprayed by MediCoat DES4000 equipment onto the surface of a pure iron stent substrate in an ultrasonic atomization spraying mode to form a zinc-containing layer, thus obtaining the vascular stent of the comparative example 2. A pumping rate of the equipment may be 0.05 mL/min, an ultrasonic intensity may be 70%, a rotation speed may be 250 r/min, an advancing speed may be 0.3 cm/s, and a stroke may be four times.

By the above-mentioned exemplary detection method, the vascular stent provided by the comparative example 2 may be measured to have a mass-to-surface area ratio of the zinc of 0.05 μg/mm$^2$, an average porosity of the zinc-containing layer of 8%, a zinc content in the zinc-containing layer of 1.4 wt. %, a thickness of the zinc-containing layer of 10 μm, and a weight average molecular weight of the polylactic acid of 500,000.

Figure 9:
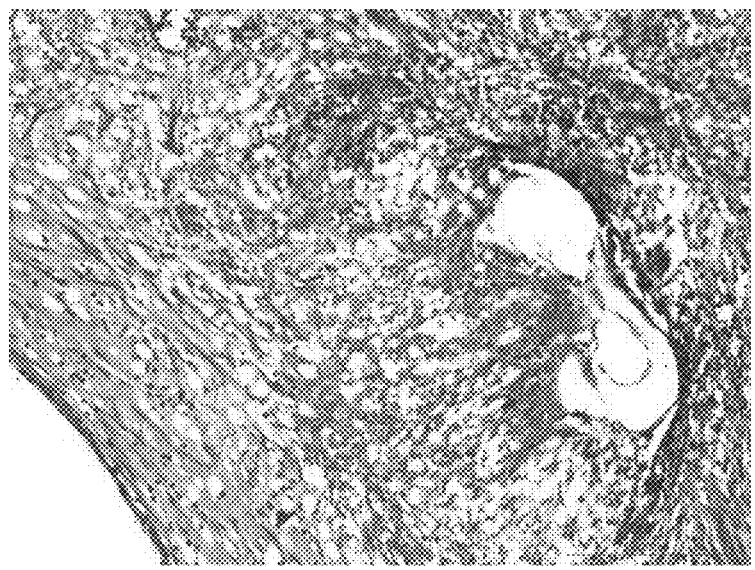
FIG. 9 is a pathological section of tissues around the vascular stent one month after an exemplary vascular stent is implanted into the coronary vessel of the minipig.

The vascular stent of comparative example 2 may be implanted into coronary vessels of a minipig, and an over-expansion ratio may be kept in a range of 1.1:1 to 1.2:1 during the implantation. After the device is implanted for one month, it could be known from the OCT measurement data that the stenosis rate of the blood vessels around the stent may be 50%, the stent and the vascular tissues around the stent may be taken out for pathological analysis, and a pathological picture may be shown in FIG. 9. The pathological analysis results may show that after the vascular stent provided by the comparative example 2 is implanted in the animal body for one month, the smooth muscle cells of the tissues around the stent may have apparent proliferation phenomenon.

The result indicates that compared with embodiment 2, in the vascular stent of the comparative example 2, the mass-to-surface area ratio of the zinc is lower, resulting in excessively lower generation rate of the zinc-containing substances in the tissues around the stent, and excessively low concentration of the zinc-containing substances accumulated in the tissues, which cannot inhibit the proliferation of the smooth muscular cells.

COMPARATIVE EXAMPLE 3

Zinc lactate and polylactic acid in a mass ratio of 3:44 may be mixed and then dissolved in a mixed solvent of ethyl acetate and ethyl alcohol in a volume ratio of 20:1 to prepare a mixed solution in which a zinc lactate concentration may be 0.3 mg/mL and a polylactic acid concentration may be 4.4 mg/mL, and the obtained mixture may be sprayed by Medi-Coat DES4000 equipment onto the surface of a pure iron stent substrate in an ultrasonic atomization spraying mode, thus obtaining the vascular stent. The pumping rate of the equipment may be 0.05 mL/min, the ultrasonic intensity may be 70%, the rotation speed may be 250 r/min, the advancing speed may be 0.3 cm/s, and the stroke may be four times.

By the above-mentioned detection method, the vascular stent provided by the comparative example 3 may be measured to have a mass-to-surface area ratio of the zinc of 300 μg/mm$^2$, an average porosity of the zinc-containing layer of 8%, a zinc content in the zinc-containing layer of 1.4 wt. %, a thickness of the zinc-containing layer of 10 μm, and a weight average molecular weight of the polylactic acid of 500,000.

The vascular stent of the comparative example 3 may be implanted into a coronary vessel of a minipig, and an overspread ratio may be kept in a range of 1.1:1 to 1.2:1 during the implantation. After the device is implanted for one month, the stent and the vascular tissues surrounding the stent may be taken out for pathological analysis. The pathological analysis results may show that after the vascular stent provided by the comparative example 3 has been implanted in the animal body for one month, the smooth muscle cells of the vascular tissues around the stent may have no apparent proliferation, but the necrosis phenomenon may have occurred.

The result indicates that compared with embodiment 2, in the vascular stent of the comparative example 3, the mass-to-surface area ratio of the zinc is relatively higher, resulting in excessively higher generation rate of the zinc-containing substances in the tissues around the stent, which causes the death of normal cells and the cell necrosis phenomenon.

COMPARATIVE EXAMPLE 4

Zinc gluconate and polylactic acid in a mass ratio of 4:11 may be mixed and then dissolved in a mixed solvent of ethyl acetate and ethanol in a volume ratio of 20:1, then the obtained mixture may be sprayed on the surface of a conventional 304 stainless steel vascular stent substrate using MediCoat DES4000 equipment in an ultrasonic atomization spraying mode, and a zinc-containing layer may be formed on the surface of the vascular stent substrate; and then polylactic acid may be sprayed on the zinc-containing layer to form a barrier layer (5 mg/mL, polylactic acid ethyl acetate solution) by an ultrasonic atomization spraying method, thus obtaining the vascular stent. When the zinc-containing layer is sprayed, a pumping rate of the equipment may be 0.09 mL/min, an ultrasonic intensity may be 70%, a rotation speed may be 250 r/min, an advancing speed may be 0.1 cm/s, and the stroke may be seven times; and when the barrier layer is sprayed, the pumping rate may be 0.04 mL/min, the ultrasonic intensity may be 50%, the rotation speed may be 250 r/min, the advancing speed may be 0.1 cm/s, and the stroke may be two times.

By the above-mentioned detection method, the vascular stent provided by the comparative example 4 may be measured to have a mass-to-surface area ratio of the zinc of 2 μg/mm$^2$, an average porosity of the zinc-containing layer of 15%, a zinc content in the zinc-containing layer of 8 wt. %, a thickness of the zinc-containing layer of 61 μm, a thickness of the barrier layer of 11 μm and a weight average molecular weight of the polylactic acid of 200,000.

The vascular stent of the comparative example 4 may be implanted into a coronary vessel of a minipig, and an over-expansion ratio may be kept in a range of 1.1:1 to 1.2:1 during the implantation. After the device is implanted for 3 months, it could be known from the OCT measurement data that the stenosis rate of the blood vessels surrounding the stent may be 65%, and the stent and vascular tissues around the stent may be taken out for pathological analysis. The pathological analysis results may show that after the vascular stent provided by the comparative example 4 has been implanted in the animal body for one month, the smooth muscle cells of the vascular tissues around the stent may have no apparent proliferation, but the cell necrosis may have occurred.

The result indicates that compared with embodiment 3, in the vascular stent of the comparative example 4, the thickness of the zinc-containing layer is relatively higher, at the same release rate, resulting in excessively higher concentration of the zinc-containing substances accumulated in the tissues around the stent after the stent is implanted for 3 months. Although the smooth muscle cells around the stent are not apparently proliferated, the cell necrosis occurs.

COMPARATIVE EXAMPLE 5

The zinc gluconate solid may be processed by a mill to obtain zinc gluconate powder having a particle size less than 5 μm. The zinc gluconate powder and polylactic acid in a mass ratio of 1:30 may be mixed and then dissolved in ethyl acetate, the concentration of the zinc gluconate may be 0.14 mg/mL, the concentration of the polylactic acid may be 4.2 mg/mL, and then the obtained mixture may be sprayed on the surface of the stent substrate made of the iron-magnesium alloy material through the MediCoat DES4000 equipment to form a zinc-containing layer, thus obtaining the vascular stent of the present comparative example. The pumping rate of the equipment may be 0.07 mL/min, the ultrasonic intensity may be 50%, the rotation speed may be 250 r/min, the advancing speed may be 0.2 cm/s, and the stroke may be four times.

By the above-mentioned detection method, the vascular stent provided by the comparative example 5 may be measured to have a mass-to-surface area ratio of the zinc of 10 μg/mm$^2$, an average porosity of the zinc-containing layer of 10%, a zinc content in the zinc-containing layer of 0.5 wt. %, a thickness of the zinc-containing layer of 25 μm, and a weight average molecular weight of the polylactic acid of 200,000.

The vascular stent of the comparative example 5 may be implanted into a coronary vessel of a minipig, and an over-expansion ratio may be kept in a range of 1.1:1 to 1.2:1 during the implantation. After the device is implanted for one month, it could be known from the OCT measurement data that the stenosis rate of the blood vessels around the stent may be 20%; after the device is implanted for 3 months, it could be known from the OCT measurement data that the stenosis rate of the blood vessel around the stent may be 70%; and the stent and vascular tissues around the stent may be taken out for pathological analysis. The pathological analysis results may show that after the vascular stent provided by the comparative example 5 has been implanted for 3 months, the smooth muscle cells of the vascular tissues around the stent may have apparent proliferation.

The result indicates that compared with embodiment 9, in the vascular stent of the comparative example 5, the zinc content of the zinc-containing layer is relatively lower, so that the release time of the zinc-containing substances is shorter under the condition of the same release rate of the zinc-containing substances. Therefore, although the stent of the comparative example 5 can inhibit the proliferation of the smooth muscular cells in the tissues around the stent after being implanted for one month, the smooth muscular cells in the tissues around the stent are still apparently proliferated after the stent is implanted for 3 months.

COMPARATIVE EXAMPLE 6

The zinc gluconate solid may be processed by a mill to obtain zinc gluconate powder having a particle size less than 5 μm. The zinc gluconate powder and polylactic acid in a mass ratio of 19:3 may be mixed and then dissolved in ethyl acetate, the concentration of the zinc gluconate may be 26.6 mg/mL, the concentration of the polylactic acid may be 4.2 mg/mL, and then the obtained mixture may be sprayed on the surface of the stent substrate made of the iron-magnesium alloy material through the MediCoat DES4000 equipment to form a zinc-containing layer, thus obtaining the vascular stent of the comparative example 6. The pumping rate of the equipment may be 0.07 mL/min, the ultrasonic intensity may be 50%, the rotation speed may be 250 r/min, the advancing speed may be 0.2 cm/s, and the stroke may be four times.

By the above-mentioned detection method, the vascular stent provided by the comparative example 6 may be measured to have a mass-to-surface area ratio of the zinc of 10 μg/mm$^2$, an average porosity of the zinc-containing layer of 10%, a zinc content in the zinc-containing layer of 95 wt. %, a thickness of the zinc-containing layer of 25 μm, and a weight average molecular weight of the polylactic acid of 200,000.

The vascular stent of the comparative example 6 may be implanted into a coronary vessel of a minipig, and an over-expansion ratio may be kept in a range of 1.1:1 to 1.2:1 during the implantation. After the device is implanted for 3 months, it could be known from the OCT measurement data that the stenosis rate of the blood vessels around the stent may be 30%, and the stent and the vascular tissues around the stent may be taken out for pathological analysis. The pathological analysis results may show that after the vascular stent provided by the comparative example 6 is implanted for 3 months, the smooth muscle cells of the vascular tissues around the stent had no apparent proliferation, but stent struts may not be subjected to the normal endothelialization.

The result indicates that compared with embodiment 9, in the vascular stent of the comparative example 6, the zinc content of the zinc-containing layer is relatively higher, so that the release time of the zinc-containing substances is longer under the condition of the same release rate of the zinc-containing substances. Therefore, when the vascular stent provided by the comparative example 6 is implanted for 3 months, the smooth muscle cells of the vascular tissues around the stent have no apparent proliferation. However, the normal endothelialization of the stent struts is affected.

In summary, according to the implantable device provided by the embodiments, by controlling the ratio of the mass of the zinc elements in the zinc-containing layer to the surface area of the implantable device and the average porosity of the zinc-containing layer, the concentration of the zinc-containing substances in the tissues around the implantable device can inhibit the proliferation of smooth muscle cells around the implantable device, and the ulceration or necrosis of the tissues around the device due to the fact that the concentration of the zinc-containing substance accumulated in the tissues is greater than the cytotoxic concentration after the device is implanted can also be avoided.

It can be understood that in the embodiments, the implementation modes are schematically illustrated only by taking the zinc-containing layer covering the entire substrate. According to the technical solutions provided herein, the zinc-containing layer can also only partially cover the surface of the substrate; or the substrate is provided with a gap, a groove or a hole, and the zinc-containing layer is arranged in the gap, the groove or the hole. In the above exemplary implementation modes, as long as the ratio of the mass of the zinc elements in the zinc-containing layer to the surface area of the implantable device and the average porosity are controlled, a purpose of inhibiting the proliferation of the smooth muscle cells of the vascular tissues around the device without causing the necrosis of normal tissue cells can be achieved.

Various technical features of the embodiments described above may be combined arbitrarily, and in order to simplify the description, all possible combinations of various technical features of the embodiments described above are not described, however, as long as there is no conflict between these technical features, they should be considered to be within the scope of the description.

The above-described embodiments illustrate only a few implementation modes of the present disclosure, the description of which is specific and detailed, but shall not be construed to limit the scope of the present disclosure. It may be contemplated that a number of variations and modifications may be made by those skilled in the art without departing from the spirit of the present disclosure, which fall within the scope of the disclosure. Therefore, the protection scope of the disclosure shall be determined by the appended claims.

The invention claimed is:

1. An implantable device, comprising:
a substrate and a zinc-containing layer at least partially covering the substrate, wherein the zinc-containing layer contains a zinc compound, wherein a ratio of a mass of zinc elements in the zinc-containing layer to a surface area of the substrate is 1 to 150 μg/mm$^2$, and an average porosity of the zinc-containing layer is 1% to 15%;
wherein the zinc compound is selected from at least one of zinc gluconate, zinc tartrate, zinc lactate, zinc carbonate, zinc hydroxide, zinc sulfate, zinc chloride, zinc phosphate, zinc nitrate, zinc glycyrrhizinate, zinc citrate, zinc amino acid, zinc acetate, sodium zincate, and zinc sulfide;
wherein a content of zinc elements in the zinc-containing layer is 1.4 wt. % to 80 wt. %; and
wherein a thickness of the zinc-containing layer is 1 μm to 50 μm, wherein the substrate is made of a degradable material, a non-degradable material, or a partially degradable material: and wherein the implantable device is a vascular stent, a biliary stent, an esophageal stent, a urethral stent, an airway stent, or a vena cava filter.

2. The implantable device according to claim 1, further comprising one or more additional zinc-containing layers; and wherein the zinc-containing layer further comprises a polymer.

3. The implantable device according to claim 2, wherein the polymer is selected from at least one of a degradable polymer, a non-degradable polymer, or at least one of copolymers formed by at least one monomer forming the degradable polymer and at least one monomer forming the non-degradable polymer,
wherein the degradable polymer is selected from at least one of polylactic acid, polyglycolic acid, polycaprolactone, polyethylene succinate, polybutylene succinate and poly(β-hydroxybutyrate), and the non-degradable polymer is selected from at least one of polystyrene, polytetrafluoroethylene, polymethyl methacrylate, polycarbonate and polyethylene terephthalate;
wherein a weight average molecular weight of the polymer is 100,000 to 500,000.

4. The implantable device according to claim 1, further comprising a barrier layer, wherein the barrier layer at least partially covers the zinc-containing layer.

5. The implantable device according to claim 4, wherein the barrier layer further comprises a polymer;
wherein a sum of a thickness of the barrier layer and a thickness of the zinc-containing layer is greater than 0 μm and less than or equal to 50 μm.

6. The implantable device according to claim 5, wherein the polymer is selected from at least one of a degradable polymer, a non-degradable polymer, or at least one of copolymers formed by at least one monomer forming the degradable polymer and at least one monomer forming the non-degradable polymer,
wherein the degradable polymer is selected from at least one of polylactic acid, polyglycolic acid, polycaprolactone, polyethylene succinate, polybutylene succinate and poly(β-hydroxybutyrate), and the non-degradable polymer is selected from at least one of polystyrene, polytetrafluoroethylene, polymethyl methacrylate, polycarbonate and polyethylene terephthalate;
wherein a weight average molecular weight of the polymer is 100,000 to 500,000.

7. An implantable device, comprising:
a substrate and a zinc-containing layer at least partially covering the substrate, wherein the zinc-containing layer contains a zinc compound, wherein a ratio of a mass of zinc elements in the zinc-containing layer to a surface area of the substrate is 1 to 150 μg/mm$^2$;
wherein the zinc compound is selected from at least one of zinc gluconate, zinc tartrate, zinc lactate, zinc carbonate, zinc hydroxide, zinc sulfate, zinc chloride, zinc phosphate, zinc nitrate, zinc glycyrrhizinate, zinc citrate, zinc amino acid, zinc acetate, sodium zincate, and zinc sulfide;
wherein an average porosity of the zinc-containing layer is 1% to 30%;
wherein a content of zinc elements in the zinc-containing layer is 1.4 wt. % to 80 wt. %; and
wherein a thickness of the zinc-containing layer is 1 μm to 50 μm, wherein the substrate is made of a degradable material, a non-degradable material, or a partially degradable material: and wherein the implantable device is a vascular stent, a biliary stent, an esophageal stent, a urethral stent, an airway stent, or a vena cava filter.

8. The implantable device according to claim 7,
wherein the implantable device further comprising one or more additional zinc-containing layers; and/or
wherein the zinc-containing layer further comprises a polymer.

9. The implantable device according to claim 8, wherein the polymer is selected from at least one of a degradable polymer, a non-degradable polymer, or at least one of copolymers formed by at least one monomer forming the degradable polymer and at least one monomer forming the non-degradable polymer,
wherein the degradable polymer is selected from at least one of polylactic acid, polyglycolic acid, polycaprolactone, polyethylene succinate, polybutylene succinate and poly(β-hydroxybutyrate), and the non-degradable polymer is selected from at least one of polystyrene, polytetrafluoroethylene, polymethyl methacrylate, polycarbonate and polyethylene terephthalate; and
wherein a weight average molecular weight of the polymer is 100,000 to 500,000.

10. The implantable device according to claim 7, further comprising a barrier layer, wherein the barrier layer at least partially covers the zinc-containing layer; and
wherein the porosity of the zinc-containing layer is 1% to 15%.

11. The implantable device according to claim 10, wherein the barrier layer further comprises a polymer; and wherein a sum of a thickness of the barrier layer and a thickness of the zinc-containing layer is greater than 0 μm and less than or equal to 50 μm.

12. The implantable device according to claim 11, wherein the polymer is selected from at least one of a degradable polymer, a non-degradable polymer, or at least one of copolymers formed by at least one monomer forming the degradable polymer and at least one monomer forming the non-degradable polymer,
wherein the degradable polymer is selected from at least one of polylactic acid, polyglycolic acid, polycaprolactone, polyethylene succinate, polybutylene succinate and poly(β-hydroxybutyrate), and the non-degradable polymer is selected from at least one of polystyrene, polytetrafluoroethylene, polymethyl methacrylate, polycarbonate and polyethylene terephthalate; and wherein a weight average molecular weight of the polymer is 100,000 to 500,000.

13. An implantable device, comprising:
a substrate and a zinc-containing layer at least partially covering the substrate, wherein the zinc-containing layer contains a zinc compound, wherein a ratio of a mass of zinc elements in the zinc-containing layer to a surface area of the substrate is 0.1 to 200 μg/mm$^2$;
wherein the zinc compound is selected from at least one of zinc gluconate, zinc tartrate, zinc lactate, zinc carbonate, zinc hydroxide, zinc sulfate, zinc chloride, zinc phosphate, zinc nitrate, zinc glycyrrhizinate, zinc citrate, zinc amino acid, zinc acetate, sodium zincate, and zinc sulfide;
wherein the implantable device further comprises a barrier layer
wherein a sum of a thickness of the barrier layer and a thickness of the zinc-containing layer is greater than 0 μm and less than or equal to 50 μm; and
wherein a content of zinc elements in the zinc-containing layer is 1.4 wt. % to 80 wt. %, wherein the substrate is made of a degradable material, a non-degradable material, or a partially degradable material: and wherein the implantable device is a vascular stent, a biliary stent, an esophageal stent, a urethral stent, an airway stent, or a vena cava filter.

14. The implantable device according to claim 13, an average porosity of the zinc-containing layer is 1% to 30%
wherein the barrier layer at least partially covers the zinc-containing layer; and/or
wherein the zinc-containing layer or the barrier layer further comprises a polymer.

15. The implantable device according to claim 14, wherein the polymer is selected from at least one of a degradable polymer, a non-degradable polymer, or at least one of copolymers formed by at least one monomer forming the degradable polymer and at least one monomer forming the non-degradable polymer,
wherein the degradable polymer is selected from at least one of polylactic acid, polyglycolic acid, polycaprolactone, polyethylene succinate, polybutylene succinate and poly(β-hydroxybutyrate), and the non-degradable polymer is selected from at least one of polystyrene, polytetrafluoroethylene, polymethyl methacrylate, polycarbonate and polyethylene terephthalate; and
wherein a weight average molecular weight of the polymer is 100,000 to 500,000.

16. The implantable device according to claim 13, further comprising one or more additional zinc-containing layers; wherein the ratio of the mass of zinc elements in the zinc-containing layer to the surface area of the substrate is 1 to 150 μg/mm$^2$; and wherein the porosity of the zinc-containing layer is 1% to 15%.

* * * * *